United States Patent
Bleakman et al.

(10) Patent No.: US 6,242,462 B1
(45) Date of Patent: Jun. 5, 2001

(54) PHARMACOLOGICAL AGENTS

(75) Inventors: David Bleakman, Zionsville, IN (US); David R. Helton, Lake Forest; Iyengar Smriti, Carmel, both of CA (US); David Lodge, Indianapolis, IN (US); Paul L Ornstein, Carmel, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/402,174

(22) PCT Filed: Apr. 6, 1998

(86) PCT No.: PCT/US98/06905

§ 371 Date: Feb. 22, 2000

§ 102(e) Date: Feb. 22, 2000

(87) PCT Pub. No.: WO98/45270

PCT Pub. Date: Oct. 15, 1998

Related U.S. Application Data

(60) Provisional application No. 60/042,795, filed on Apr. 7, 1997.

(51) Int. Cl.⁷ .................................................. A61K 31/47
(52) U.S. Cl. ............................................ 514/307; 546/147
(58) Field of Search .............................. 514/307; 540/147

(56) References Cited

U.S. PATENT DOCUMENTS

| | | | |
|---|---|---|---|
| 5,446,051 | 8/1995 | Ornstein | 514/307 |
| 5,670,516 | 9/1997 | Arnold | 514/307 |
| 5,731,348 | * 3/1998 | Gu | 514/561 |

FOREIGN PATENT DOCUMENTS 0 590 789   8/1993   (EP) .

OTHER PUBLICATIONS

Bleakman D., et al., Pharmacological Discrimination of GluR5 and GluR6 Kainate Receptor Subtypes by ( 3S, 4aR, 6R, 8aR)–6–[2–(2)H–tetrazole–5–yl)ethyl]decahydroisoquinoline–3 carboxylic–acid, vol. 49(4), 1996 pp. 581–585.

Clarke V.R.J., et al., "A hippocampal GluR5 Kainate receptor regulating inhibitory synaptic transmission" Nature, MacMillan Journals Ltd. London, GB vol. 389, 1977, pp. 599–603.

* cited by examiner

*Primary Examiner*—James H. Reamer
(74) *Attorney, Agent, or Firm*—Alexander Wilson

(57) ABSTRACT

Antagonists selective for the GluR5 receptor are useful for the treatment of pain. Also disclosed are novel decahydroisoquinoline derivatives which are selective GluR5 receptor antagonists.

4 Claims, No Drawings

PHARMACOLOGICAL AGENTS

This application is a 371 of PCT/US98/06905 filed Apr. 6, 1998, and also claims benefit of Provisional No. 60/042,795 filed Apr. 7, 1997.

The present invention relates to a new class of glutamate receptor antagonists useful for the treatment of pain.

L-Glutamate mediates excitatory neurotransmission in the mammalian central nervous system through its action at glutamate receptors. There are two broad classes of glutamate receptors, known as the ionotropic glutamate receptor and the metabotropic glutamate receptor. Within the class of ionotropic glutamate receptor are three classes, known as the N-methyl-D-aspartate (NMDA), (R,S)-2-amino-3-(3-hydroxy-5-methyl-isoxazol-4-yl)propanoate (AMPA) and kainate (KA) receptors. Molecular biological studies have established that AMPA receptors are composed of subunits (GluR1-4) that can assemble to form functional channels. Five kainate receptors, classified as either high affinity (KA1 and KA2) or low affinity (GluR5, GluR6 and GluR7) kainate receptors have been identified. (Bleakman et al, *Molecular Pharmacology*, 1996, Vol. 49, No. 4, pgs. 581–585).

European Patent Application Publication No. 590789A1 and U.S. Pat. No. 5,446,051 disclose that certain decahydroisoquinoline derivatives are AMPA receptor antagonists, and as such are useful in the treatment of many different conditions, including pain. There is no disclosure of any compound actually being tested for use in the treatment of pain.

Surprisingly, it has now been found that a compound within the scope of European Patent Application Publication No. 590789A1, namely (3S,4aR,6S,8aR)-6-[(1(2)H-tetrazol-5-yl)methoxymethyl]decahydroisoquinoline-3-carboxylic acid, is a selective GluR5 antagonist and is effective in animal models of pain. It is therefore believed that a new pharmacological class of agents, represented by (3S,4aR,-6S,8aR)-6-[(1(2)H-tetrazol-5-yl)methoxymethyl] decahydro-isoquinoline-3-carboxylic acid, has been found for the treatment of pain.

According to one aspect, therefore, the present invention provides a method for the treatment of pain, which comprises administering to a mammal in need of treatment an effective amount of a selective GluR5 receptor antagonist.

According to another aspect, the present invention provides the use of a selective GluR5 receptor antagonist for the manufacture of a medicament for the treatment of pain.

GluR5 receptor antagonists may be identified by radiolabelled ligand binding studies at the cloned and expressed human GluR5 receptor (Korczak et al., 1994, Recept. Channels 3; 41–49), by whole cell voltage clamp electrophysiological recordings of functional activity at the human GluR5 receptor (Korczak et al., 1994, Recept. Channels 3; 41–49) and by whole cell voltage clamp electrophysiological recordings of currents in acutely isolated rat dorsal root ganglion neurons (Bleakman et al., 1996, *Mol. Pharmacol.* 49; 581–585).

The selectivity of compounds acting at GluR5 receptors may be determined by measurement of activity at other AMPA and kainate receptors including receptor-ligand binding studies and whole-cell voltage clamp electrophysiological recordings of functional activity at human GluR1, GluR2, GluR3 and GluR4 receptors (Fletcher et al., 1995, Recept. Channels 3; 21–31), receptor-ligand binding studies and whole-cell voltage clamp electrophysiological recordings of functional activity at human GluR6 receptors (Hoo et al., Recept. Channels 2; 327–338) and whole-cell voltage clamp electrophysiological recordings of functional activity at AMPA receptors in acutely isolated cerebellar Purkinje neurons (Bleakman et al., 1996, *Mol. Pharmacol.* 49; 581–585) and other tissues expressing AMPA receptors (Fletcher and Lodge, 1996, *Phannacol. Ther.* 70; 65–89).

Preferably, the selective GluR5 receptor antagonist has a binding affinity of at least 10 fold greater for GluR5 than that for other glutamate receptors, more preferably at least 100 fold greater.

The selective GluR5 antagonist for use according to the invention may be a single compound or combination of compounds capable of functioning as an antagonist that is selective for the GluR5 receptor over other ionotropic glutamate receptors. For example, it may be a combination of a compound capable of functioning as an antagonist at the GluR5 receptor and one or more other glutamate receptors in combination with one or more compounds capable of blocking its actions at the one or more other ionotropic glutamate receptors. Preferably, the selective GluR5 antagonist is a single compound.

The following compounds have been found to be selective GluR5 receptor antagonists and are therefore preferred for use according to the invention: 3SR,4aRS,6SR,8aRS-6-((((1H-tetrazole-5-yl)methyl)oxy)methyl)-1,2,3,4,4a,5,6,7,8,8a-decahydroisoquinoline-3-carboxylic acid, 3S,4aR,6S,8aR-6-((((1H-tetrazole-5-yl)methyl)oxy)methyl)-1,2,3,4,4a,5,6,-7,8,8a-decahydroisoquinoline-3-carboxylic acid, 3SR,4aRS,6SR,8aRS-6-(((4-carboxy)phenyl)methyl)-1,2,3,4,4a,5,6,7,8, 8a-decahydroisoquinoline-3-carboxylic acid and 3S,4aR,6S,8aR-6-(((4-carboxy)phenyl)methyl)-1,2,3,4,4a,-5,6,7,8,8a-decahydroisoquinoline-3-carboxylic acid.

The results of evaluating the activity of the aforementioned decahydroisoquinoline derivatives at the GluR5 receptor and other ionotropic glutamate receptors in the tests described above are given in Tables 1 and 2 below.

TABLE 1

Selectivity Profile for Compounds of the Invention in Binding Studies

Cell lines (HEK293 cells) stably transfected with human GluR5 receptors were employed. Displacement of 3H AMPA by increasing concentrations of test compound was used on GluR1–4-expressing cells and 3H kainate (KA) on GluR5 and expressing cells. Estimated activity (Ki) in nM was as follows.

| Test Compound | G1uR1 | G1uR2 | G1uR3 | G1uR4 | G1uR5 | G1uR6 |
|---|---|---|---|---|---|---|
| A* | 150686 ± 49789 (3) | 35337 ± 6163 (3) | 47793 ± 8770 (3) | 31606 ± 5914 (3) | 3061 ± 1038 (3) | 6 ± 5% displ @ 100 μM (3) |

-continued

| Test Compound | GluR1 | GluR2 | GluR3 | GluR4 | GluR5 | GluR6 |
|---|---|---|---|---|---|---|
| B* | — | — | — | — | 5823 (2) | — |
| C* | 21% at 1 mM | 55% at 1 mM | — | 23% at 1 mM | 6810 | — |

A - 3SR, 4aRS, 6SR, 8aRS-6-[(1(2)H-tetrazol-5-yl)methoxy-methyl]decahydroisoquinoline-3-carboxylic acid (average of 3 results)
B - Compound of Example 1 (average of 2 results)
C - 3SR, 4aRS, 6SR, 8aRS-6-(((4-carboxy)phenyl)methyl)-1,2,3-4,4a,5,6,7,8,8a-decahydroisoquinoline-3-carboxylic acid (one result only)
D - Compound of Example 2
— Not tested

TABLE 2

Selectivity Profile for Compounds of the Invention in Electrophysioloaical Studies Functional studies were carried out on HEK293 cells stably transfected with human GluR receptors and on acutely isolated dorsal root ganglion neurons (DRG) using patch-clamp technology (Bleakman et al., 1996, *Mol. Pharmacol.*, 49, 581–585). IC50 values ($\mu$M) for test Compound A were estimated for GluR1–4 vs 100 $\mu$M AMPA and GluR5 and GluR6 vs 100 $\mu$M KA with the following results:

| Test Compound | GluR1 | GluR2 | GluR3 | GluR4 | GluR5 | GluR6 | DRG* |
|---|---|---|---|---|---|---|---|
| A | >100 | >100 | >100 | >100 | 3.9 ± 0.5 | >100 | 0.60 ± 0.06 |
| D | — | — | — | >100 | — | >100 | 0.98 ± 0.07 |

*Based on % inhibition of 30 $\mu$M kainate induced current.

The forms of pain which may be treated according to the invention include severe, chronic, intractable and neuropathic pain.

The compounds 3S,4aR,6S,8aR-6-((((1H-Tetrazole-5-yl)methyl)oxy)methyl)1,2,3,4,4a,5,6,7,8,8a-decahydroisoquinoline-3-carboxylic acid; and 3S,4aR,6S,8aR-6-(((4-carboxy)phenyl)methyl)1,2,3,4,4a,5,6,7,8,8a-decahydroisoquinoline-3-carboxylic acid and their pharmaceutically acceptable salts are believed to be novel and are provided as a further aspect of the invention. The invention also provides a pharmaceutical composition comprising one of these compounds and a pharmaceutically acceptable diluent or carrier. They may be prepared, and formulated into pharmaceutical compositions, by the general methods described in European Patent Application No. 590789A1 and U.S. Patent No. 5,446,051.

The ability of selective GluR5 receptor antagonists to treat pain in mammals may be demonstrated using the well known formalin, tail flick and acetic acid-induced writhing tests.

1) Formalin Test

Male Sprague-Dawley rats (200–250 g; Charles River, Portage, Mich.) were housed in group cages and maintained in a constant temperature and a 12h light/12h dark cycle 4–7 days before the studies were performed. Animals had free access to food and water at all times prior to the day of the experiment.

Drugs or vehicles were administered intraperitoneally (i.p.) or orally (p.o.) by gavage in a volume of 1 ml/kg.

The test was performed in custom made Plexiglas® boxes 25×25×20× cm in size (according to Shibata et al., Pain 38; 347–352, 1989, Wheeler-Aceto et al., Pain, 40; 229–238, 1990). A mirror placed at the back of the cage allowed the unhindered observation-of the formalin injected paw. Rats were acclimated individually in the cubicles at least 1 hour prior to the experiment. All testing was conducted between 08:00 and 14:00 h and the testing room temperature was maintained at 21–23° C. Test compounds were administered 30 minutes prior to the formalin injection. Formalin (50 $\mu$l of a 5% solution in saline) was injected subcutaneously into the dorsal lateral surface of the right hind paw with a 27 gauge needle. Observation started immediately after the formalin injection. Formalin-induced pain was quantified by recording in 5 minute intervals the number of formalin injected paw licking events and the number of seconds each licking event lasted. These recordings were made for 50 minutes after the formalin injection.

Different scoring parameters have been reported for the formalin test. The total time spent licking and biting the injected paw was demonstrated to be most relevant (Coderre et al., *Eur. J. Neurosci.* 6; 1328–1334, 1993; Abbott et al., Pain, 60; 91–102, 1995) and was chosen for the testing score. The early phase score is the sum of time spent licking in seconds from time 0 to 5 minutes. The late phase was scored in 5 minute blocks from 15 minutes to 40 minutes and is expressed accordingly or also by adding the total number of seconds spent licking from minute 15 to minute 40 of the observation period. Data are presented as means with standard errors of means (± SEM). Data were evaluated by one-way analysis of variance (ANOVA) and the appropriate contrasts analyzed by Dunnett "t" test for two sided comparisons. Differences were considered to be significant if the P-value was less than 0.05 and indicated by asterisk. Statistics were determined at the 5 minute time point and at 5 minute intervals between 15 and 40 minutes. Where data are expressed as total amount of time spent licking in the late phase, statistics were performed on the total time spent licking as well and are indicated accordingly.

In this test, the compound of Example 1 was found to be active at doses in the range 10 to 100 mg/kg in reducing second phase paw licking time.

2) Tail Flick Test

This well known test measures the effect of a test compound on the time taken for an animal to flick its tail out of a focused beam of light. In the test, a beam of light from a lamp is focused on a surface, and the lamp is then switched off. Treated and untreated (control) animals are restrained, with their tails positioned at the focal point of the beam of light from the lamp. The lamp is then switched on, and the time taken for the animal's tail to respond by moving is recorded.

Subcutaneous administration of the compound of Example 1 in mice at doses of 3, 10, and 30 mg/kg produced a dose dependent increase in response time. Oral administration of the same compound at doses of 0.03, 0.1, 0.3 and 3 mg/kg to cynomolgous primates also produced a dose dependent increase in response time. These data show that the compound of Example 1, which is a selective GluR5 antagonist, is effective at treating pain, and has unexpected oral activity in cynomolgous primates.

3) Acetic acid induced mouse writhing test.

This test measures the ability of a test compound to reduce the amount of writhing induced by intraperitoneal injection of acetic acid in mice.

Doses of test compound or control are administered to male CD-1 mice. Each animal is then administered 0.5% acetic acid in a volume of 0.01 mg/g intraperitoneally. The animals are then placed in individual plexiglas observation chambers and the total number of writhes (flattening of the abdominal wall and asymmetric stretching and extending of the body and hindlimbs) recorded between 5 and 10 minutes after acetic acid administration.

The compound of Example 1 was administered at a dose of 1, 3, 10 and 30 mg/kg, and produced a dose dependent reduction in writhing.

The particular dose of antagonist administered according to this invention will of course be determined by the particular circumstances surrounding the case, including the activity of the particular antagonist administered, the route of administration, the particular condition being treated, and similar considerations. The antagonist can be administered by a variety of routes including oral, rectal, transdermal, subcutaneous, intravenous, intramuscular, or intranasal routes. Alternatively, the antagonist may be administered by continuous infusion. A typical daily dose will contain from about 0.001 mg/kg to about 100 mg/kg of the antagonist. Preferably, daily doses will be about 0.05 mg/kg to about 50 mg/kg$_7$ more preferably from about 0.1 mg/kg to about 20 mg/kg.

The following examples illustrate the preparation of novel compounds that are selective GluR5 antagonists.

Tetrahydrofuran was dried by distillation from sodium. All other solvents and reagents were used as obtained. The reactions were generally monitored for completion using thin layer chromatography (TLC). Thin layer chromatography was performed using E. Merck Kieselgel 60 $F_{254}$ plates, 5 cm ×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Elemental analyses for carbon, hydrogen and nitrogen were determined on a Control Equipment Corporation 440 Elemental Analyzer. "Chromatography" refers to flash chromatography (Still, WC; Kahn, M; Mitra, A. *J. Org. Chem.* 1978, 43, 2923) on 230–400 mesh Silica Gel 60, using the amount of silica gel and solvent of elution referred to parenthetically in the text. "Cation exchange chromatography" refers to ion exchange with Dowex 50X-8 (100–200) resin (H$^+$ form). The resin was prepared by washing (in a coarse porosity sintered glass funnel) with water, then methanol, then water, then 3N ammonium hydroxide (pH $^3$12), then water, then 1N HCl (pH$^2$1), then water until the pH is neutral. The resin was packed into a glass column in water, and the compound (which is dissolved in water at a pH between 2 and 7) was slowly eluted onto the resin, then the column washed with water until the pH is neutral, then 50% aqueous THF, then water. The compound is eluted off of the resin with 10% aqueous pyridine, and product containing fractions (which are detected with ninhydrin stain on a TLC plate) are combined and concentrated in vacuo. Water is added and the mixture concentrated in vacuo. This procedure is repeated two more times, and ensures complete removal of pyridine.

EXAMPLE 1

3S,4aR,6S,8aR-6-((((1H-Tetrazole-5-yl)methyl)oxy)methyl)-1,2,3,4,4a,5,6,7,8,8a-decahydroisoquinoline-3-carboxylic Acid A. Ethyl 3S,4aR,6S,8aR 6-(((Cyanomethyl)oxy)methyl)-2-methoxycarbonyl-1,2,3,4,4a,5,6,7,8,8a-decahydroisoquinoline-3-carboxylate: A solution of 12.8 g (42.6 mmol) of ethyl 3S,4aR,6S,8aR-6-hydroxymethyl-2-methoxycarbonyl-1,2,3,4,-4a,5,6,7,8,8a-decahydroisoquinoline-3-carboxylate (Ornstein, et al., *Journal of Organic Chemistry*, 1994, 59, 7862–7869), 10.6 g (85.3 mmol) of ((methoxy)ethoxy)methyl chloride 16.5 g (127.9 mmol) of N,N-diisopropylethylamine and 20 mg of 4-N,N-dimethylaminopyridine in 70 mL of methylene chloride was heated to reflux for four hours, then cooled, diluted with 150 mL of ether and washed twice with 100 mL each of 10% aqueous sodium bisulfate. The organic phase was dried (magnesium sulfate), filtered, and concentrated in vacuo. The residual oil was dissolved in 70 mL of methylene and treated with 17.0 mL (12.7 g, 127.9 mmol) of trimethylsilyl cyanide, then the solution was cooled to 0° C. and treated with 1.3 mL (1.5 g, 10.7 mmol) of boron trifluoride etherate. The resulting solution was allowed to warm to room temperature. After three hours at room temperature, the reaction mixture was treated with 100 mL of 10% aqueous potassium carbonate, then 150 mL of ether. The phases were separated and the organic phase washed one more time with 100 mL of 10% aqueous potassium carbonate. The organic phase was dried (magnesium sulfate), filtered, and concentrated in vacuo. Chromatography of the residue (350 g of silica gel, 30% ethyl acetate/hexane) afforded 11.9 g (83%) of the title compound. Analysis calculated for $C_{17}H_{26}N_2O_5$: C, 60.34; H, 7.74; N, 8.28. Found: C, 60.06; H, 7.69; N, 8.31.

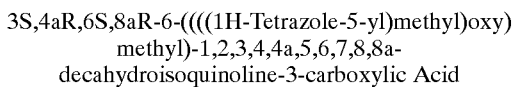

$[\alpha]_D = -33.5°$ (c =1, CH$_2$Cl$_2$).

B. A mixture of 11.7 g (34.6 mmol) of the compound from Example 1A and 23.0 g (69.2 mmol) of tributyltin azide was heated to 100° C. for five days. The mixture was treated with 100 mL of 6 N hydrochloric acid, and heated continued at 100° C. After about 18 hours, the reaction mixture was allowed to cool to room temperature, then extracted with 50 mL of ether, 50 mL of dichloromethane and 50 mL of ether, then the aqueous phase was concentrated in vacuo. Cation exchange chromatography of the residue afforded a solid that was suspended in acetone, refluxed for one hour, then filtered and washed with acetone and ether, and dried in vacuo at 60° C. to afford 8.5 g (83%) of the title compound. Analysis calculated for $C_{13}H_{21}N_5O_3 \cdot 0.33\ C_3H_6O$: C, 52.43; H, 7.44; N, 21.84. Found: C, 52.74; H, 7.22; N, 21.50.

$([\alpha]_D = -21.6°\ (c = 1,\ 1N\ HCl))$.

EXAMPLE 2

Preparation of 3S,4aR,6S,8aR-6-(((4-carboxy)phenyl)methyl)-1,2,3,4,4a,5,6,7,8,8a-decahydroisoquinoline-3-carboxylic acid A. Methyl 4-(diethylphosphonomethyl)benzoate: A solution of 25.0 g (110 mmol) of methyl 4-bromomethylbenzoate and 37 mL (36.3 g, 220 mmol) of triethyl phosphite in 150 mL of toluene was heated for 18 hours at reflux, then cooled and concentrated in vacuo. Chromatography (400 g of silica gel, ethyl acetate) of the residue afforded 30.6 g (98%) of the title compound.

B. Ethyl 3S,4aR,6S,8aR-6-(((4-methoxycarbonyl)phenyl)-methyl)-1,2,3,4,4a,5,6,7,8,8a-decahydroisoquinoline-3-carboxylate: 14.1 g (49.4 mmol) of the compound from Example 2A and 48 mL (of a 1.0 M solution) of sodium bis(trimethyl-silyl)amide in 100 mL of THF was stirred 45 min at 0° C., then treated with 10.0 g of ethyl 3S,4aR,8aR-6-oxo-2-methoxy-carbonyl-1,2,3,4,4a,5,6,7,8,8a-decahydroisoquinoline-3-carboxylate in 40 mL of THF. After 15 minutes at 0° C., the reaction was quenched with 100 mL of water and extracted three times with 150 mL each of ether. The combined organics were dried (magnesium sulfate), filtered and concentrated in vacuo. The residue was dissolved in 500 mL of ether, treated with 3.0 g of 5% palladium on carbon, and hydrogenated at room temperature and one atmosphere of hydrogen for 24 hours. The mixture was diluted with 500 mL of ether, filtered through a pad of diatomaceous earth, and the filtrate concentrated in vacuo. Chromatography (400 g of silica gel, 25% ethyl acetate/hexane) of the residue afforded 12.0 g (81%) of the title compound, as a mixture of methyl and ethyl esters from transesterification of the methyl ester during hydrogenation.

C. 12.0 g of the compound from Example 2B was heated to reflux for 18 hours with 100 mL of 6N hydrochloric acid, then cooled to room temperature. The resulting solid was filtered, washing with water, acetone and ether, and dried in vacuo at 60° C. to afford 6.2 g (57%) of the title compound. Analysis calculated for $C_{18}H_{23}NO_4 \cdot HCl \cdot 1.25\ H_2O$: C, 57.44; H, 7.10; N, 3.72. Found: C; 57.44; H, 6.69; N, 3.76.

$[\alpha]_D = -4.8°\ (c = 1,\ 1N\ HCl)$.

We claim:
1. A method for the treatment of pain, which comprises administering to a mammal in need of treatment an effective amount of a selective GluR5 receptor antagonist.
2. A method as claimed in claim 1, in which the selective GluR5 receptor antagonist is selected from 3SR,4aRS,-6SR,8aRS-6-((((1H-tetrazole-5-yl)methyl)oxy)methyl)-1,2,3,4,4a,5,6,7,8,8a-decahydroisoquinoline-3-carboxylic acid, 3S,4aR,6S,8aR-6- ((((1H-tetrazole-5-yl)methyl)oxy)methyl)1,2,3,4,4a,5,6,7,8,8a-decahydroisoquinoline-3-carboxylic acid, 3SR,4aRS,6SR, 8aRS-6- (((4-carboxy)phenyl)methyl)-1,2,3,4,4a,5,6,7,8,8a-decahydroisoquinoline-3-carboxylic acid and 3S,4aR,6S,8aR-6-(((4-carboxy)-phenyl)methyl)1,2,3,4,4a,5,6,7,8,8a-decahydro-isoquinoline-3-carboxylic acid.
3. A compound which is selected from 3S,4aR,6S,8aR-6-((((1H-tetrazole-5-yl)methyl)oxy)methyl)-1,2,3,4,4a,5,6,7,8,8a-decahydroisoquinoline-3-carboxylic acid and 3S,4aR,6S,8aR-6-(((4-carboxy)phenyl)methyl)-1,2,3,4,4a,5,6,7,8,8a-decahydroisoquinoline-3-carboxylic acid, and their pharmaceutically acceptable salts.
4. A pharmaceutical composition, which comprises a compound as claimed in claim 3 and a pharmaceutically acceptable diluent or carrier.

\* \* \* \* \*